(12) United States Patent
Alshemari

(10) Patent No.: US 8,475,454 B1
(45) Date of Patent: Jul. 2, 2013

(54) ELECTROSURGICAL MIDLINE CLAMPING SCISSORS

(76) Inventor: Hasan M. Sh. Sh. Alshemari, Saad Al-Abdulla (KW)

( * ) Notice: Subject to any disclaimer, the term of this patent is extended or adjusted under 35 U.S.C. 154(b) by 0 days.

(21) Appl. No.: 13/587,199

(22) Filed: Aug. 16, 2012

Related U.S. Application Data

(63) Continuation of application No. 13/410,109, filed on Mar. 1, 2012.

(51) Int. Cl.
*A61B 18/12* (2006.01)
(52) U.S. Cl.
USPC .............................. 606/51; 606/52
(58) Field of Classification Search
USPC .................... 606/27, 34, 41, 51, 52
See application file for complete search history.

(56) References Cited

U.S. PATENT DOCUMENTS

| | | | |
|---|---|---|---|
| 6,102,909 A * | 8/2000 | Chen et al. ...................... | 606/45 |
| 6,132,429 A * | 10/2000 | Baker ............................. | 606/50 |
| 6,162,220 A * | 12/2000 | Nezhat ........................... | 606/48 |
| 6,174,309 B1 * | 1/2001 | Wrublewski et al. ............ | 606/45 |
| 6,443,970 B1 * | 9/2002 | Schulze et al. ................. | 606/171 |
| 6,773,434 B2 * | 8/2004 | Ciarrocca ....................... | 606/51 |
| 7,041,102 B2 * | 5/2006 | Truckai et al. .................. | 606/51 |
| 7,329,257 B2 * | 2/2008 | Kanehira et al. ................ | 606/52 |
| 2002/0107517 A1 * | 8/2002 | Witt et al. ........................ | 606/50 |
| 2005/0101945 A1 * | 5/2005 | Sakurai et al. .................. | 606/29 |
| 2005/0171533 A1 * | 8/2005 | Latterell et al. ................. | 606/48 |

OTHER PUBLICATIONS

Prior art cited in U.S. Appl. No. 13/410,109, filed Mar. 1, 2012, the priority of which is claimed herein.

* cited by examiner

*Primary Examiner* — Michael Peffley
*Assistant Examiner* — Daniel Fowler
(74) *Attorney, Agent, or Firm* — Richard C. Litman

(57) ABSTRACT

The electrosurgical midline clamping scissors includes a pair of elongate arms pivotal about each other at a common axis. Each arm includes a finger loop at one end and a jaw at the opposite end. Each jaw includes a midline cutting section and a grasping section on either side of a cutting blade in the cutting section. A wire is operatively connected from a generator to each arm to transmit electricity or radio frequency through electrical conductors inside the arms. The electrical conductors extend into the jaws to form a bipolar configuration. During use, as the jaws close, the jaws complete the circuit and simultaneously clamp, cut and electrocoagulate the target tissue.

3 Claims, 5 Drawing Sheets

ELECTROSURGICAL MIDLINE CLAMPING SCISSORS

CROSS-REFERENCE TO RELATED APPLICATIONS

This is a continuation of my prior application Ser. No. 13/410,109, filed Mar. 1, 2012 now pending.

BACKGROUND OF THE INVENTION

1. Field of the Invention

The present invention relates to surgical instruments, and particularly to an electrosurgical midline clamping scissors that simultaneously cuts and electrocoagulates the incision.

2. Description of the Related Art

During surgical operation, electrocauterization is a process in which the tissue or blood vessel being cut is applied with electrical or radio frequency energy at the incision site to fuse or seal the cut ends by heat. In order to provide this energy, an instrument capable of conducting electricity must be placed at that site. The conductive instrument may have one electrode (monopolar) that cooperates with a remote conductive body plate electrode, or the instrument may have two closely spaced electrodes (bipolar).

There are two main actions that a surgeon must exercise extensively in both open and endoscopic surgery: precision of incisions, and control of bleeding. The former is wholly dependent upon the experience, skill and knowledge of the surgeon, while the latter is usually facilitated by special instruments. In the past, a surgeon would perform cuts with scissors and induce coagulation by clamping the cut ends or the desired area with surgical forceps. This is a time-consuming process, since the surgeon must manipulate two different instruments at separate times. In some instances, time can be a critical factor for the survival of the patient if the bleeding at the incision is not controlled in time. Prolonged surgical procedures also increase risks due to increasing probability of surgeon mistakes. The longer the surgery lasts, the surgeon becomes more prone to procedural mistakes from physical and mental exhaustion.

More recent developments in electrocoagulation and electrocauterization include electrosurgical instruments, such as combination bipolar scissors and forceps. These types of instruments eliminate much of the time-consuming aspects of the above cut-and-coagulate procedure. However, most are complex in construction and/or tend to require at least two steps to perform. One of these instruments utilizes two separate triggers, one trigger to actuate the forceps and clamp the desired target area, and the other trigger to actuate the cutter. Another similar combination bipolar instrument includes forceps features at a distal end from the cutting blades of the scissors. While the functionality of clamping and cutting exists in this type of device, both functions cannot be performed simultaneously.

Thus, an electrosurgical midline clamping scissors solving the aforementioned problems is desired.

SUMMARY OF THE INVENTION

The electrosurgical midline clamping scissors includes a pair of elongate arms pivotal about each other at a common axis. Each arm includes a finger loop at one end and a jaw at the opposite end. Each jaw includes a midline cutting section and a grasping section on either side of a cutting blade in the cutting section. A wire is operatively connected from a generator to each arm to transmit electricity or radio frequency through electrical conductors inside the arms. The electrical conductors extend into the jaws to form a bipolar configuration. During use, as the jaws close, the jaws complete the circuit and simultaneously clamp, cut and electrocoagulate the target tissue. A monopolar configuration is also described.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
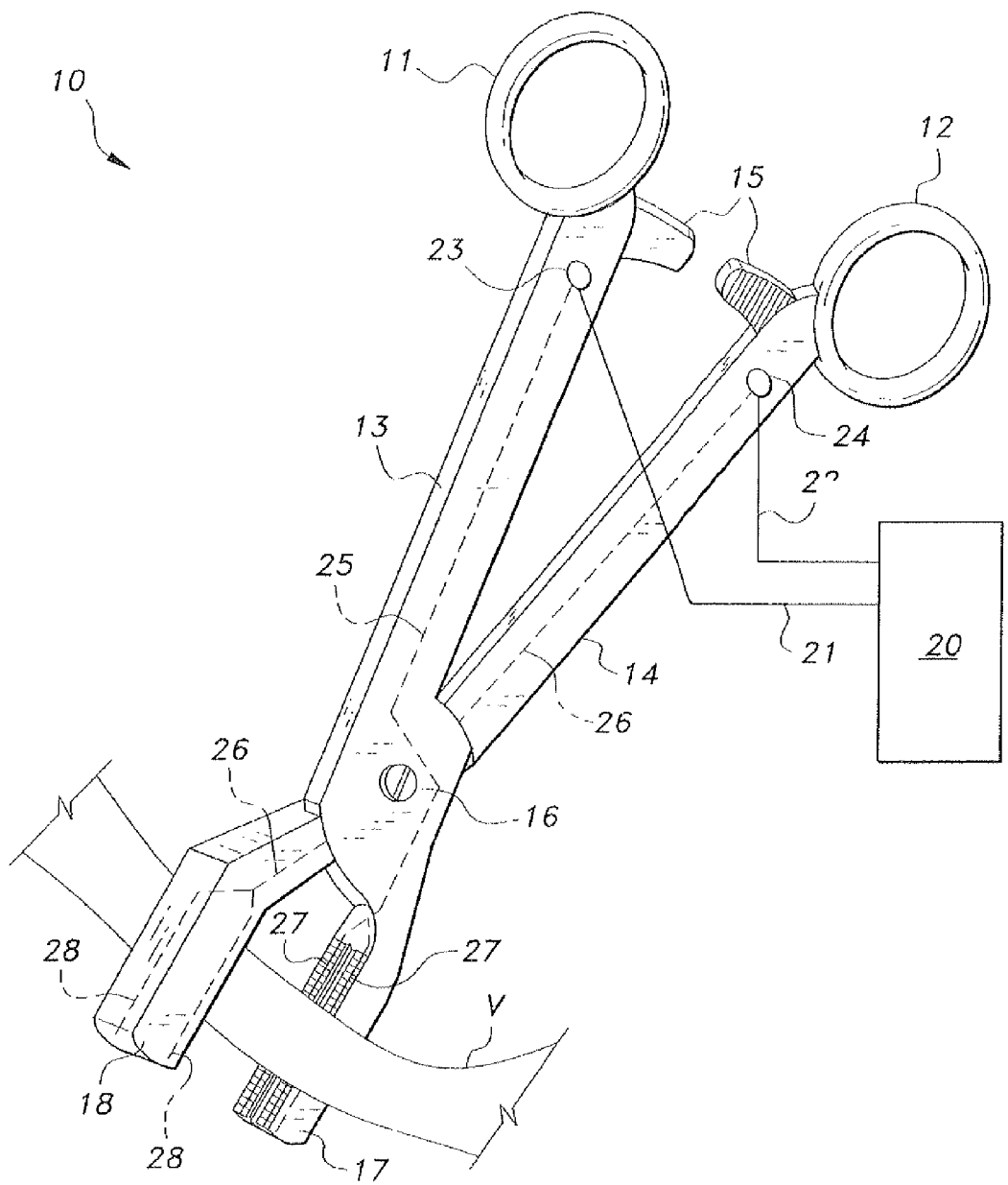
FIG. 1 is an environmental, perspective view of an electrosurgical midline clamping scissors according to the present invention.
Figure 2:
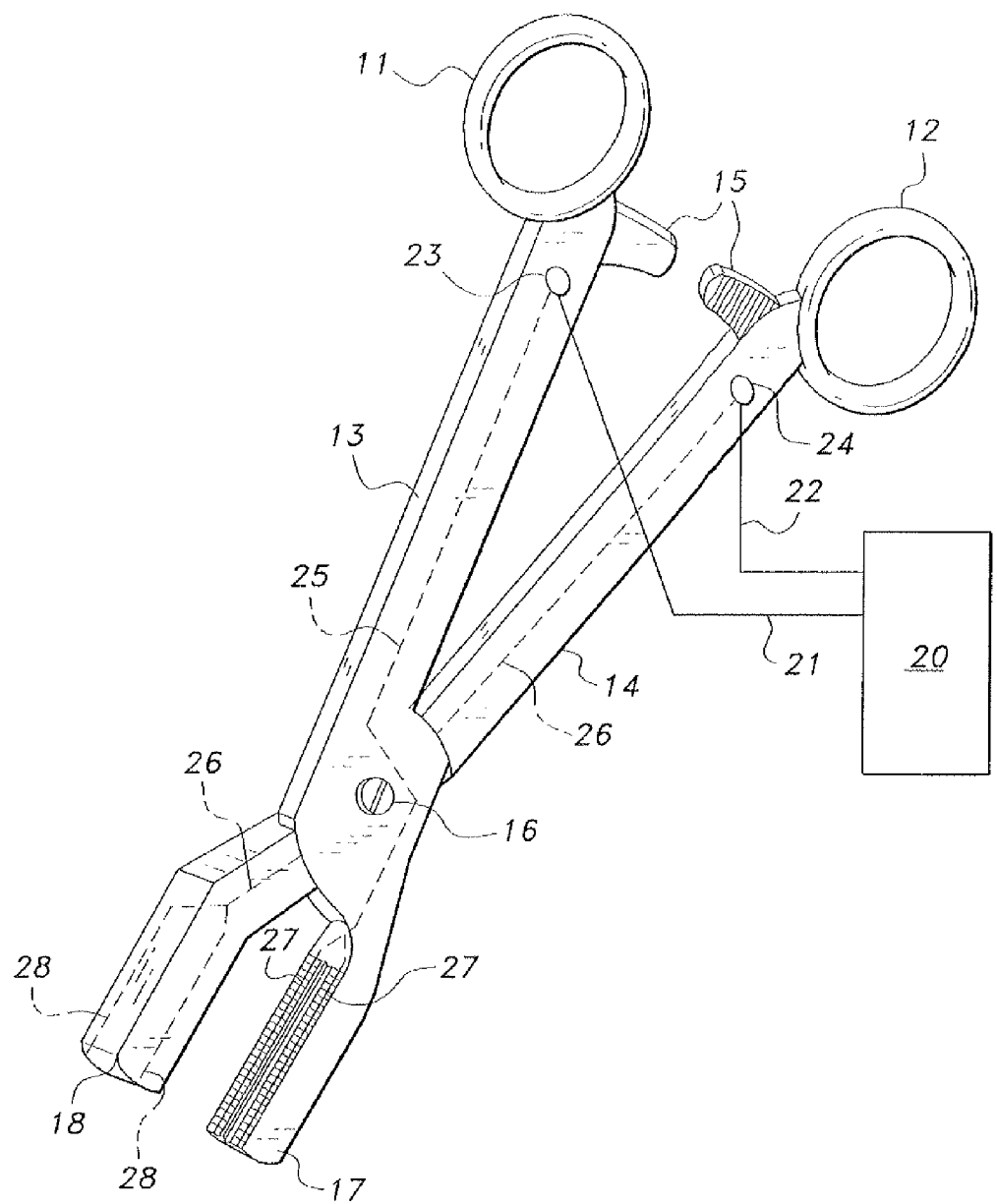
FIG. 2 is a perspective view of the electrosurgical midline clamping scissors shown in FIG. 1.
Figure 3:
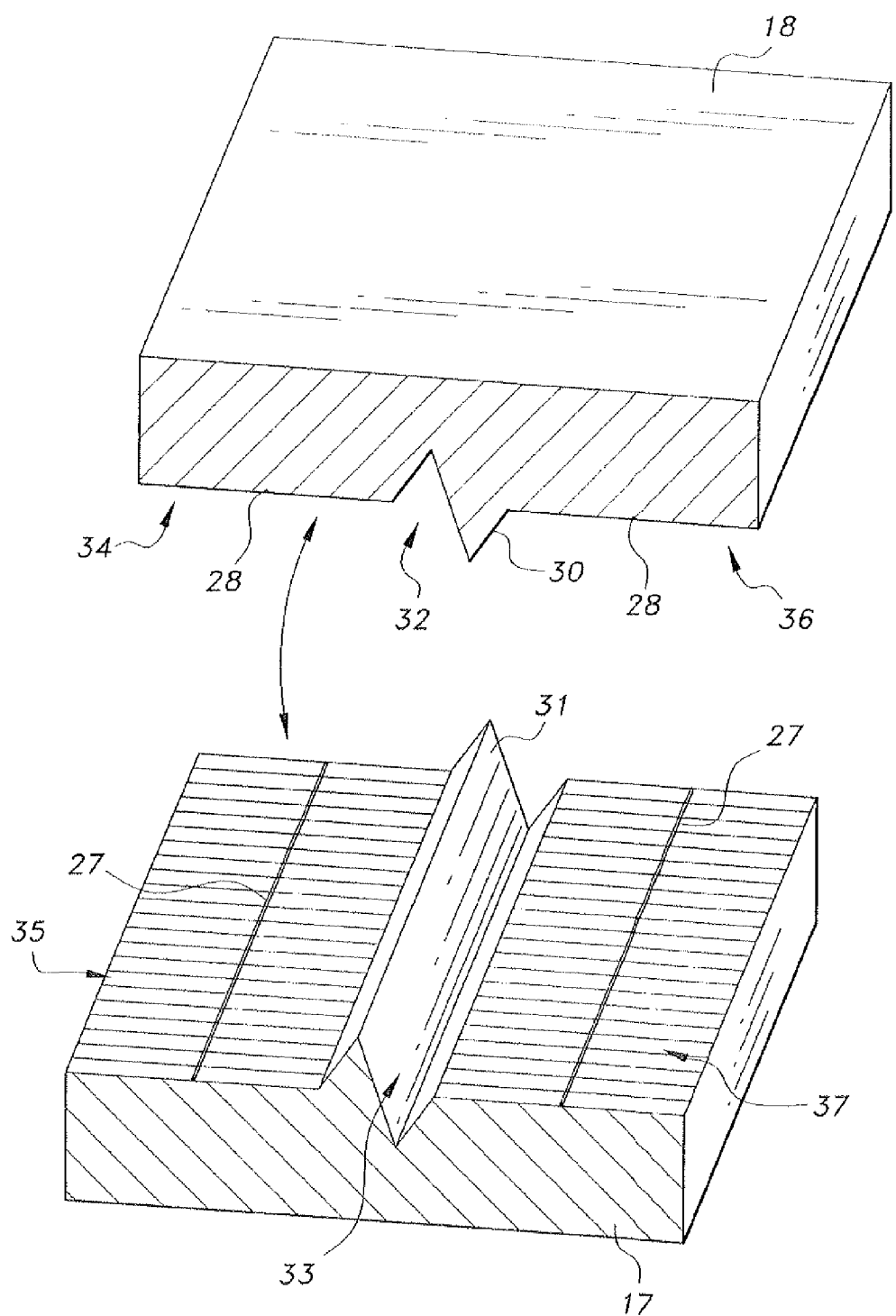
FIG. 3 is an enlarged perspective view in section of the jaws of an electrosurgical midline-clamping scissors according to the present invention.

As shown in FIGS. 1-3, in a first embodiment, the electrosurgical midline clamping scissors are configured to simultaneously clamp, electrocoagulate and cut tissue or blood vessels thereby minimizing the time required to perform the procedure. In this embodiment, the electrosurgical midline clamping scissors 10 is configured as a bipolar instrument.

As shown in FIGS. 1 and 2, the electrosurgical midline clamping scissors includes first and second finger loops 11, 12 connected to the proximal end of respective first and second, elongate arms 13, 14. Each loop is of a size to accept a thumb or finger within the loop. A conventional locking ratchet mechanism 15, similar to the locking mechanism of a hemostat, extends from or near the junction of the first and second finger loops 11, 12 and the first and second arms 13, 14.

The first and second arms 13, 14 intersect at, and are pivotal about, a pivot pin joint 16 for providing rotating motion about a common axis. The two elongate arms 13 and 14 terminate in a pair of opposed first and second jaws 17 and 18 at the distal or opposite end of the arms 13, 14.

As mentioned previously, the electrosurgical midline clamping scissors 10 is a bipolar instrument because a bipolar configuration is generally preferred in order to minimize electrical current travel. A generator 20 or other current source is disposed apart or remote from the main instrument and generates the radio frequency or electric energy required for the electrocoagulation. First and second wires 21, 22 extend from the generator. The first wire 21 is connected to a first terminal 23 on the first arm 13, while a second wire 22 is connected to a second terminal 24 on the second arm 14. Each arm 13, 14 includes a respective first electrical conductor 25 and a second electrical conductor 26 extending from the terminals 23, 24. Each electrical conductor 25, 26 (e.g., an insulated wire) extends through a lumen in the scissor arms 13, 14 into the respective, mating first and second jaws 17, 18. These electrical conductors 25, 26 can be integrally formed in the arms 13, 14 by molding, chemical vapor deposition, and the like. Alternatively, the generator wires 21, 22 may extend through openings in the arms 13, 14 and continue through channels or lumens within the arms 13, 14, to the jaws 17, 18. As shown in the drawings, the radio frequency or electrical energy from the generator 20 or current source is transported through the wires 21, 22 to the terminals 23, 24. From there, the frequency or energy travels through the electrical conductors 25, 26 in the arms 13 and 14 to the grasping surfaces of both jaws 17 and 18.

Since the electrosurgical midline clamping scissors 10 functions in a similar manner to live electrodes, some safety measures must be taken into account. To protect the user from electrical shock and unwanted burn to the surrounding tissue close to the target vessel V or target tissue in a patient, a covering or coating of insulating material can be provided on the finger loops 11 and 12, the elongate arms 13 and 14, the pivot pin 16, and the outer surface of the jaws 17 and 18. Alternatively, the electrical connecters 25, 26 extending through the lumen of the elongated arms 13 and 14 and reaching the grasping surfaces of both jaws 17 and 18 can also be similarly covered or coated with insulation.

As shown in FIGS. 2 and 3, each jaw 17 and 18 is a mirror image of the other. The first jaw 17 includes a midline cutting section having a protruding cutting blade 31 extending a substantial length of the first jaw 17 and a longitudinal groove 33 adjacent thereto. Similarly, the upper, second jaw 18 includes a protruding cutting blade 32 and adjacent longitudinal groove 34. In use, as the first blade 31 and the second blade 32 close toward each other so that the cutting edge of the first cutting blade 31 extends into the second longitudinal groove 34, while the cutting edge of the second cutting blade 32 extends into the first longitudinal groove 33 in the same manner to facilitate and complete the cut.

Each jaw 17, 18 also includes grasping sections disposed on either side of the midline cutting section. As shown, the first jaw 17 includes a first grasping section 35 disposed on one lateral side of the midline cutting section and a second grasping section 37 disposed on the other side of the midline cutting section. The electrical conductor 25 from the first arm 13 branches into electrical sub-conductors 27 or electrodes that extend into the first and second grasping sections 35, 37. Similarly, the second jaw 18 also includes a first grasping section 34, a second grasping section 36, and branching electrical sub-conductors 28 or electrodes from the electrical conductor 26. Each grasping section 34, 35, 36, 37 is provided with a textured surface, e.g., serrations, protrusions, ribs, knurled surfaces, etc., that can firmly and securely grasp the target tissue V on either side of the midline cutting sections during the incision.

In use, the jaws 17 and 18 are placed in an open position by moving the handle portions or the finger loops 11 and 12 away from each other. Once one of the jaws 17, 18 is placed under the target tissue V, the finger loops 11, 12 are moved towards each other, which correspondingly moves the jaws 17, 18 towards each other. As the jaws 17, 18 move into a closed position, the target tissue or blood vessel is simultaneously grasped by the grasping sections 34, 35, 36, 37 on either side of the cutting blades 30, 31 and cut thereby. Concurrently, electric current or radio frequency passing from one electrode, e.g., the electrical sub-conductors 28, to the other, e.g., the electrical sub-conductors 27, closes an electric circuit and produces sufficient heat to seal blood vessels or to coagulate blood vessels in the tissue. Thus, simultaneous clamping, cutting and electrocoagulation can be performed in one action, saving the surgeon considerable time compared to conventional handling of multiple surgical instruments.

Figure 4:
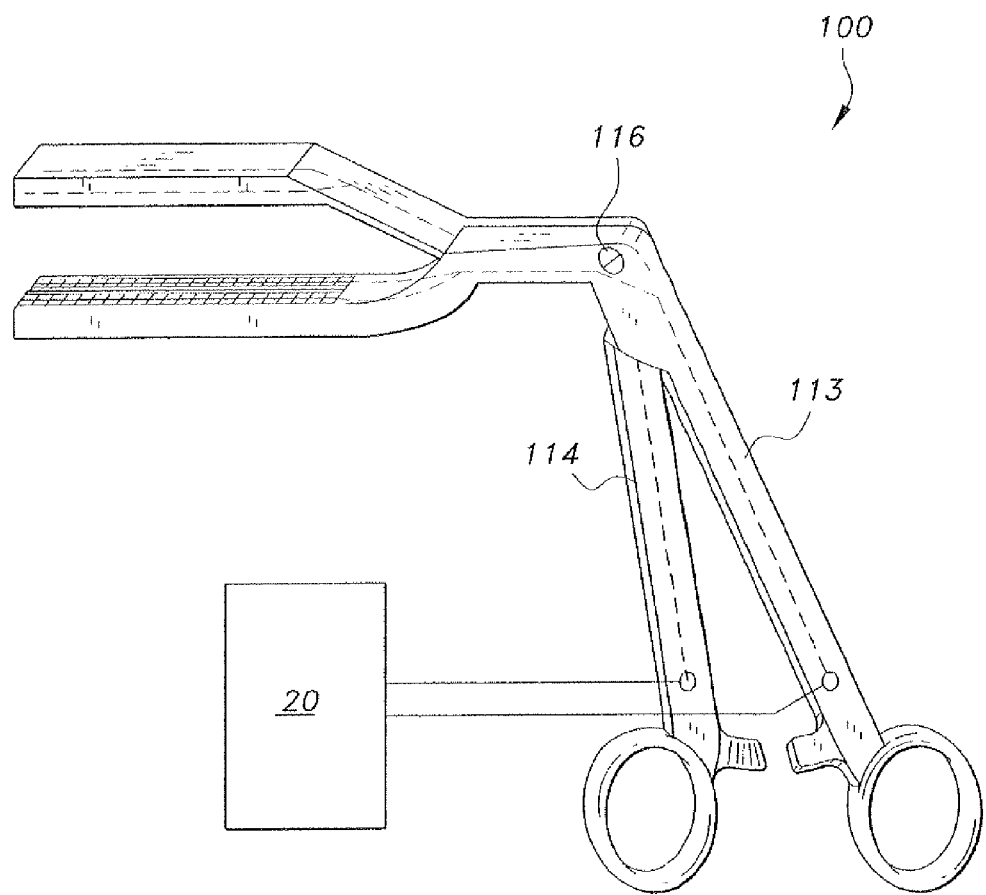
FIG. 4 is a perspective view of an alternative embodiment of electrosurgical midline clamping scissors according to the present invention.

An alternative embodiment of electrosurgical midline clamping scissors 100 is shown in FIG. 4. In this embodiment, the midline clamping scissors 100 is configured to assist the surgeon or user in reaching areas difficult to reach or manipulate with the straight configuration of the electrosurgical midline clamping scissors 10. Since the electrosurgical midline clamping scissors 100 is substantially similar to previously described, the main differences will be highlighted by reference number. It should be understood that any features not mentioned or referenced by reference number are to be incorporated from the previous embodiment.

As shown, the electrosurgical midline clamping scissors 100 is configured the same as the previous embodiment, except for the first elongate arm 113 and the second elongate arm 114. Each arm 113, 114 is bent or angled at or near the pivot pin joint 116. With this configuration, the surgeon or user can hold the electrosurgical midline clamping scissors 100 in the conventional horizontal position, while the jaws point downward. This is preferable in certain procedures, such as partial removal of the inferior turbinate in the nasal cavity or in endoscopic surgery, with different lengths and sizes.

Figure 5:
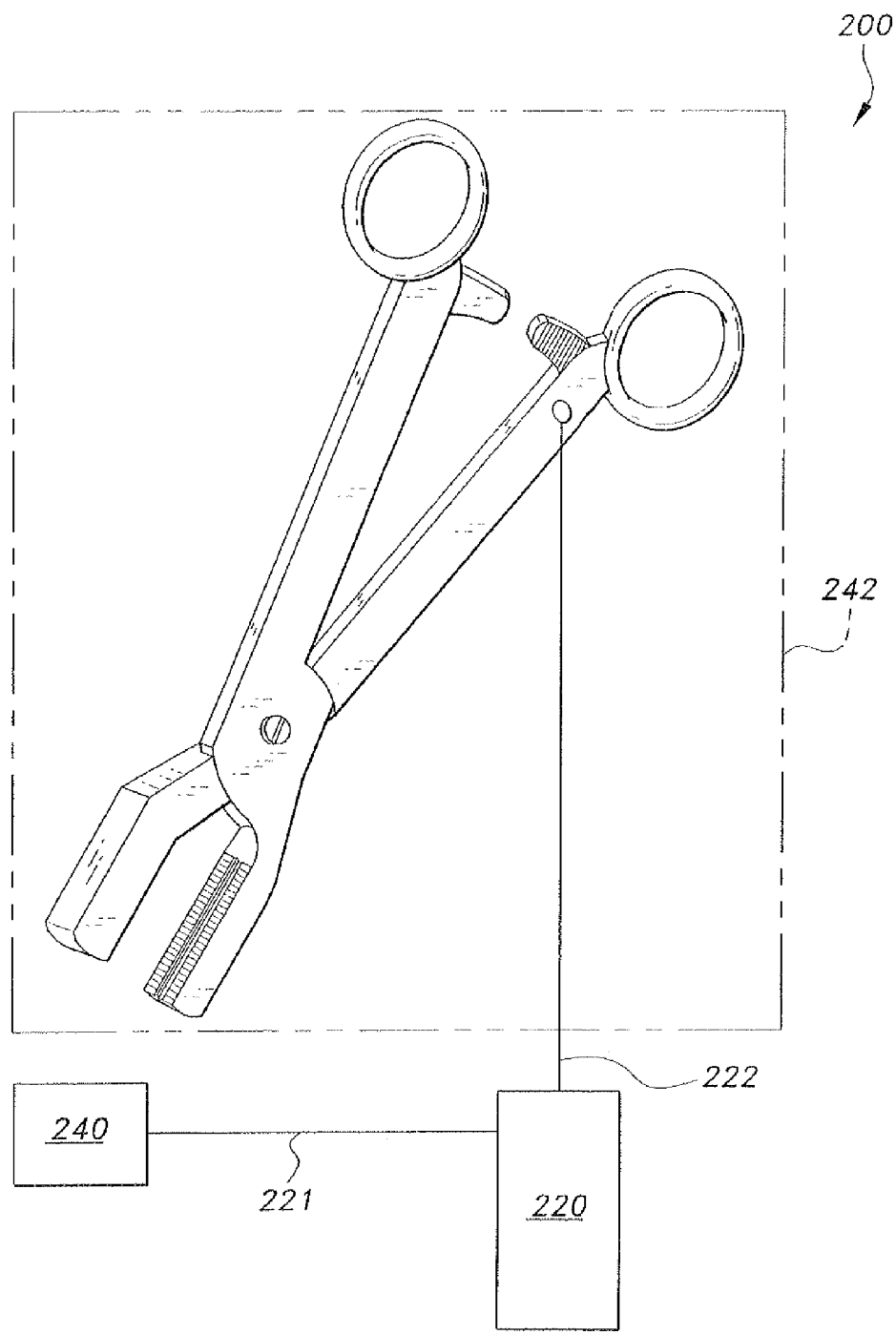
FIG. 5 is a perspective view of another alternative embodiment of electrosurgical midline clamping scissors according to the present invention.

A still further alternative embodiment is shown in FIG. 5. In this embodiment, the electrosurgical midline clamping scissors 200 is configured as a monopolar electrosurgical instrument, instead of the bipolar configuration of the previous embodiments. The electrosurgical midline clamping scissors 200 does not include any of the electrical conductors mentioned above. Instead, the generator 220 or current source includes a line or wire 222 connected to the electrosurgical midline clamping scissors 200 and another line or wire 221 connected to a remote, conductive body plate electrode 240 that completes the circuit whenever the scissors 200 is in operation. The electrosurgical midline clamping scissors 200 function as a conductor. As with the previous embodiments, the finger loops, elongate arms, pivot pin and the outer surface of the jaws are covered or coated with insulating material, as diagrammatically indicated by reference number 242. The angled electrosurgical midline clamping scissors 100 described can be similarly configured to operate as a monopolar electrosurgical instrument.

It is to be understood that the present invention is not limited to the embodiments described above, but encompasses any and all embodiments within the scope of the following claims.

I claim:

1. An electrosurgical midline clamping scissors for simultaneous mechanical cutting and electrocoagulating of tissue or blood vessels, comprising:

a pair of arms including first and second substantially elongate arms, each of the arms having a proximal end and a distal end;

a pivot joint connecting the first and second arms medially, the pivot joint defining a common axis for pivoting movement of the first and second arms with respect to each other;

a finger loop disposed at the proximal end of each of the arms, the finger loop being adapted for receiving thumbs and fingers of a user for manipulating the elongate arms;

a jaw connected to the distal end of each of the arms, each of the jaws having an elongate midline cutting section for cutting target tissue and an elongate, serrated grasping section disposed on both lateral sides of the cutting section, the jaws being movable between a spaced, open position and a closed position by pivotal movement of the first and second arms, the grasping sections being adapted for holding and clamping the target tissue during use, wherein the jaws comprise;

complementary, immovable first and second jaw surfaces;

the midline cutting section of the first jaw surface having an elongate cutting blade and an adjacent longitudinal groove, the cutting blade having an elongate cutting edge;

the midline cutting section of the second jaw surface having an elongate cutting blade and an adjacent longitudinal groove, the cutting blade having an elongate cutting edge and being the mirror image of the first jaw cutting blade and longitudinal groove; wherein the first blade extends into the second longitudinal groove and the second blade extends into the first longitudinal groove when the jaws are closed to complete mechanical cutting the target tissue between the blades;

a locking mechanism disposed between the finger loops of the elongate arms;

a generator for producing an electric current, each of the arms having a terminal, the generator having lines to each of the terminals; and an electrical conductor disposed inside each of the arms, each of the electrical conductors extending from the terminals through the arms to the respective jaws and being disposed on both lateral sides of the cutting section;

wherein closing of the jaws about the target tissue completes an electric circuit and simultaneously clamps, cuts and electrocoagulates the target tissue.

2. The electrosurgical midline clamping scissors according to claim 1, wherein each of said first and second arms is bent near said pivot joint.

3. The electrosurgical midline clamping scissors according to claim 1, further comprising an insulating coating disposed over said finger loops, said elongate arms, said pivot joint, and an outer surface of said jaws to prevent electric shock and electrical burns.

* * * * *